US012805478B2

(12) United States Patent
Wahlquist

(10) Patent No.: US 12,805,478 B2
(45) Date of Patent: Nov. 24, 2026

(54) SNAP PEA VARIETY SUGAR 204

(71) Applicant: Syngenta Crop Protection AG, Basel (CH)

(72) Inventor: Daniel James Wahlquist, Nampa, ID (US)

(73) Assignee: SYNGENTA CROP PROTECTION AG, Basel (CH)

( * ) Notice: Subject to any disclaimer, the term of this patent is extended or adjusted under 35 U.S.C. 154(b) by 66 days.

(21) Appl. No.: 18/959,775

(22) Filed: Nov. 26, 2024

(65) Prior Publication Data

US 2026/0144222 A1 May 28, 2026

(51) Int. Cl.
*A01H 6/54* (2018.01)
*A01H 5/10* (2018.01)

(52) U.S. Cl.
CPC ............... *A01H 6/546* (2018.05); *A01H 5/10* (2013.01)

(58) Field of Classification Search
None
See application file for complete search history.

(56) References Cited

U.S. PATENT DOCUMENTS 8,426,687 B2 * 4/2013 Moser .................... A01H 6/546 800/300
9,603,330 B2 3/2017 Wahlquist

OTHER PUBLICATIONS

Haun et al. The composition and origins of genomic variation among individuals of the soybean reference cultivar Williams 82. ( 2011) Plant Physiology; vol. 155; pp. 645-655 (Year: 2011).*
Grobkincky et al. Plant phenomics and the need for physiological phenotyping across scales to narrow the genotype-to-phenotype knowledge gap. (2015) J. of Exp. Botany; vol. 66; pp. 5429-5440 (Year: 2015).*
USDA; Applying for a Plant Variety Certificate of Protection (2026) dowloaded from www.ams.usda.gov/services/pvpo/ application-help/ apply on Feb. 11, 2026; pp. 1-3 (Year: 2026).*
UPOV; Explanatory notes on essentially derived varieties under the 1991 Act of the UPOV Convention (2023) International Union for the Protection of New Varieties of Plant; pp. 1-15 (Year: 2023).*
Ex Parte C (1992) Board of Patent Appeals and Interferences; 27 USPQ 2d 1492(BPAI), 1992 WL515817; pp. 1-11 (Year: 1992).*
Ex Parte McGowen (2020) Patent Trial and Appeal Board; Appeal 2019-006060 for U.S. Appl. No. 14/996,093; pp. 1-21 (Year: 2020).*
US PVP Certificate No. 202300085 issued Mar. 29, 2024 'Sugar 162'.

* cited by examiner

*Primary Examiner* — Cathy Kingdon
(74) *Attorney, Agent, or Firm* — Karen A. Magri

(57) ABSTRACT

The present invention provides novel snap pea cultivar Sugar 204 and plant parts, seed, and tissue culture therefrom. The invention also provides methods for producing a pea plant by crossing the pea plants of the invention with themselves or another pea plant. The invention also provides pea plants produced from such a crossing as well as plant parts, seed, and tissue culture therefrom.

24 Claims, No Drawings

SNAP PEA VARIETY SUGAR 204

FIELD OF THE INVENTION

This invention is in the field of pea plants, in particular, the invention relates to novel snap pea cultivar Sugar 204.

BACKGROUND OF THE INVENTION

The present invention relates to a snap pea (*Pisum sativum* var. *macrocarpon*) variety designated Sugar 204.

Garden peas (*Pisum sativum* L.) produce pod fruits and include common green English peas and edible-podded peas. These can be distinguished in that English peas are generally shelled and only the seed eaten, whereas the edible-podded peas are eaten whole. Edible-podded peas include snap peas, which are characterized by a round pod, and the flat-podded snow pea. The pods of edible-podded peas are less fibrous than those from English peas and do not open when ripe.

Pea is an important and valuable vegetable crop for both the fresh and processed markets. Thus, there is an ongoing need for improved pea varieties.

SUMMARY OF THE INVENTION

According to the invention, there is provided a novel snap pea cultivar designated herein as Sugar 204, also known as SL3204. Thus, the invention also encompasses the seeds of pea cultivar Sugar 204, the plants of pea cultivar Sugar 204, plant parts of the pea cultivar Sugar 204 (including pods, berries, seeds, gametes), methods of producing seed from pea cultivar Sugar 204, and methods for producing a pea plant by crossing the pea cultivar Sugar 204 with itself or another pea plant, methods for producing a pea plant containing in its genetic material one or more transgenes and/or locus conversions, and the transgenic and/or converted pea plants produced by that method. The invention also relates to methods for producing other pea plants derived from pea cultivar Sugar 204 and to pea plants, parts thereof and seed produced using those methods. The present invention further relates to pea seeds and plants (and parts thereof including pods and/or berries) produced by crossing pea cultivar Sugar 204 with itself or with another pea plant (e.g., an F1 hybrid seed or plant).

In another aspect, the present invention provides regenerable cells for use in tissue culture of pea cultivar Sugar 204. In embodiments, the tissue culture is capable of regenerating plants having all or essentially all of the physiological and morphological characteristics of the foregoing pea plant and/or of regenerating plants having the same or substantially the same genotype as the foregoing pea plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules, pods, berries and/or seeds as well as callus and/or protoplasts derived from any of the foregoing. Still further, the present invention provides pea plants regenerated from the tissue cultures of the invention.

In representative embodiments, an exemplary pea plant according to the invention comprises cells comprising at least one set of chromosomes of pea cultivar Sugar 204. Optionally, the pea plant can be an inbred plant or a hybrid plant.

As a further aspect, the invention provides a method of producing pea seed, the method comprising crossing a plant of pea cultivar Sugar 204 with itself or a second pea plant and allowing seed to form. Pea cultivar Sugar 204 can be the female and/or male parent. Optionally, the method further comprises collecting the seed.

The invention further provides a method of producing a progeny pea plant, the method comprising crossing a plant of pea cultivar Sugar 204 with itself or a second pea plant to produce at least a first progeny plant, which may optionally be a selfed plant or an F1 hybrid. Pea cultivar Sugar 204 can be the female and/or male parent.

Another aspect of the invention provides methods for producing hybrids and other pea plants derived from pea cultivar Sugar 204. Pea plants derived by the use of those methods are also part of the invention as well as plant parts, seed, gametes and tissue culture from such hybrid or derived pea plants.

In embodiments, a pea plant or population of pea plants derived from pea cultivar Sugar 204 comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pea cultivar Sugar 204, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pea cultivar Sugar 204, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and/or double haploid technology. Optionally, the derived pea plant can be an inbred plant, a hybrid plant or a double haploid plant. In embodiments, the pea plant derived from pea cultivar Sugar 204 is one, two, three, four, five or more breeding crosses removed from pea cultivar Sugar 204.

In embodiments, a hybrid or derived plant from pea cultivar Sugar 204 comprises a desired added trait(s). In representative embodiments, a pea plant derived from pea cultivar Sugar 204 comprises all of the morphological and physiological characteristics of pea cultivar Sugar 204 (e.g., as described herein, in particular, in Tables 1 to 3). In embodiments, the pea plant derived from pea cultivar Sugar 204 comprises an additional desired added trait(s) and otherwise all or essentially all of the morphological and physiological characteristics of pea cultivar Sugar 204 (e.g., as described herein, in particular, in Tables 1 to 3). Optionally, the pea plant can be an inbred plant, a hybrid plant, or a double haploid plant.

The invention also relates to methods for producing a pea plant comprising in its genetic material one or more transgenes and to the transgenic pea plant produced by those methods (and progeny pea plants comprising the transgene). Also provided are plant parts, seed and tissue culture from such transgenic pea plants, optionally wherein one or more cells in the plant part, seed, or tissue culture comprises the transgene. The transgene can be introduced via plant transformation and/or breeding techniques (e.g., conventional breeding from an initial transformed plant(s)).

In another aspect, the present invention provides for converted plants of pea cultivar Sugar 204, which comprise one or more single locus conversions. Plant parts, seed, and tissue culture from such converted plants are also contemplated by the present invention. A single locus conversion may be a dominant, semi-dominant or recessive allele. In representative embodiments, the single locus confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, male sterility, enhanced nutritional quality, improved appearance (e.g., color), improved salt tolerance, industrial usage, or any combination thereof. A single converted locus may be a naturally occurring pea locus, a genome-edited locus, a mutated locus, or a transgene introduced into pea through genetic engineering techniques.

The invention further provides methods for developing pea plants in a pea plant breeding program using plant breeding techniques including, for example, recurrent selection, backcrossing, pedigree breeding, double haploid techniques, restriction fragment length polymorphism enhanced selection, genetic marker enhanced selection, genome editing and/or transformation. Seeds, pea plants, and parts thereof, produced by such breeding methods are also part of the invention.

The invention also provides methods of multiplication or propagation of pea plants of the invention, which can be accomplished using any method known in the art, for example, via vegetative propagation, grafting and/or seed.

The invention further provides a method of producing food or feed comprising (a) obtaining a pea plant of the invention, optionally wherein the plant has been cultivated to maturity, and (b) collecting at least one pea plant or part thereof (e.g., pods or berries) from the plant. In embodiments, obtaining a pea plant comprises growing the plant.

Additional aspects of the invention include harvested products and processed products from the pea plants of the invention. A harvested product can be a whole plant or any plant part, as described herein. Thus, in some embodiments, a non-limiting example of a harvested product includes a seed, a pod, a berry and/or a shoot.

In representative embodiments, a processed product includes, but is not limited to: dehydrated, cut, sliced, ground, pureed, dried, canned, jarred, washed, brined, sprouted, packaged, refrigerated, frozen, heated and/or cooked pods, berries, seeds and/or shoots of the pea plants of the invention, or any other part thereof. In embodiments, the processed product includes washed and packaged pods, berries and/or shoots (or parts thereof) of the invention, for example, in a canned or frozen form.

Thus, the invention also provides a method of producing a processed product from a plant of the invention, the method comprising (a) obtaining a pod, berry or shoot of a plant of the invention; and (b) processing the pod, berry or shoot to produce a processed product. In embodiments, processing comprises canning, jarring and/or freezing.

The invention provides seed of the pea plants of the instant invention. In representative embodiments, the invention provides a seed of a pea plant of the invention. In embodiments, the invention is directed to seed that produces the pea plants of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of pea cultivar Sugar 204.

As a further aspect, the invention provides a plant of pea cultivar Sugar 204.

As an additional aspect, the invention provides a pea plant, or a part thereof, having all or essentially all of the physiological and morphological characteristics of a plant of pea cultivar Sugar 204.

As another aspect, the invention provides pods, berries, seed and/or shoots of the pea plants of the invention and a processed product from the pods, berries, seed and/or shoots of the inventive pea plants.

As still another aspect, the invention provides a method of producing pea seed, the method comprising crossing a pea plant of the invention with itself or a second pea plant. The invention also provides seed produced by this method and plants produced by growing the seed.

As yet a further aspect, the invention provides a method for producing pea seed, the method comprising: (a) crossing a pea plant of the invention with itself or a second pea plant; and (b) allowing seed to form. In embodiments, the method is practiced to produce seeds of pea cultivar Sugar 204 (e.g., seed increase) by crossing the plant with itself, e.g., by open pollination. The invention also provides seed produced by this method and plant, and part thereof including pods, berries and shoots, produced by growing the seed.

As yet a further aspect, the invention provides a method for producing a seed of a pea plant derived from pea cultivar Sugar 204, the method comprising: (a) crossing a pea plant of pea cultivar Sugar 204 with a second (different) pea plant; and (b) allowing seed of a pea plant derived from pea cultivar Sugar 204 to form. In embodiments, the method further comprises: (c) growing a plant from the seed derived from pea cultivar Sugar 204 of step (b); (d) selfing the plant of step (c) or crossing it to a second pea plant to form additional pea seed derived from pea cultivar Sugar 204, and (e) optionally repeating steps (c) and (d) one or more times to generate further derived pea seed from pea cultivar Sugar 204, wherein in step (c) a plant is grown from the additional pea seed of step (d) in place of growing a plant from the seed of step (b). In embodiments, the method comprises: (e) repeating steps (c) and (d) one or more times (e.g., one to three, one to five, one to six, one to seven, one to ten, three to five, three to six, three to seven, three to eight or three to ten times) to generate further derived pea seed. As another option, the method can comprise collecting the seed. The invention also provides seed produced by these methods and pea plants produced by growing the seed, which can optionally be inbred or hybrid plants.

As another aspect, the invention is also directed to a method of producing a pod comprising obtaining a plant according to the instant invention and harvesting a pod from the plant. In embodiments, obtaining a plant of the invention comprises growing the plant to produce a pod. In one embodiment, the method further comprises processing the pod to obtain a berry or seed. In one embodiment, a berry according to the instant invention is a fresh product or a processed product (e.g., a canned product or a frozen product).

The invention is also directed to a method of producing a berry or seed comprising obtaining a pod of a plant according to the instant invention and processing the pod to obtain a berry or seed. In one embodiment, a berry according to the instant invention is a fresh product or a processed product (e.g., a canned product or a frozen product).

Still further, as another aspect, the invention provides a method of vegetatively propagating a plant of pea cultivar Sugar 204. In a non-limiting example, the method comprises: (a) collecting tissue capable of being propagated from a plant of pea cultivar Sugar 204; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into pea cultivar Sugar 204, the method comprising: (a) crossing a first plant of pea cultivar Sugar 204 with a second pea plant that comprises a desired trait to produce $F_1$ progeny; (b) selecting an $F_1$ progeny that comprises the desired trait; (c) crossing the selected $F_1$ progeny with pea cultivar Sugar 204 to produce backcross progeny; and (d) selecting backcross progeny comprising the desired trait to produce a plant derived from pea cultivar Sugar 204 comprising a desired trait.

In embodiments, the selected progeny has one or more of the characteristics of Sugar 204 (e.g., as described herein, in particular, in Tables 1 to 3). In embodiments, the selected progeny comprises all or essentially all the morphological and physiological characteristics of pea cultivar Sugar 204. Optionally, the method further comprises: (e) repeating steps (c) and (d) one or more times (e.g., one, two, one to three, one to five, one to six, one to seven, one to ten, three to five, three to six, three to seven, three to eight or three to ten times) to produce a plant derived from pea cultivar Sugar 204 comprising the desired trait, wherein in step (c) the selected backcross progeny produced in step (d) is used in place of the selected F1 progeny of step (b).

In representative embodiments, the invention also provides a method of producing a plant of pea cultivar Sugar 204 comprising a desired added trait, the method comprising introducing a transgene conferring the desired trait into a plant of pea cultivar Sugar 204. The transgene can be introduced by transformation methods (e.g., genetic engineering) or breeding techniques (e.g., crossing pea cultivar Sugar 204 with a transformed plant or a plant that is descended from a transformed plant and comprises the transgene). In embodiments, the plant comprising the transgene has one or more of the morphological and physiological characteristics of Sugar 204 (e.g., as described herein, in particular, in Tables 1 to 3). In embodiments, the plant comprising the transgene comprises all or essentially all of the morphological and physiological characteristics of pea cultivar Sugar 204.

The invention also provides pea plants produced by the methods of the invention or a selfed progeny thereof, wherein the pea plant has the desired added trait as well as seed from such pea plants The invention also provides seed that produces the plants derived from pea cultivar Sugar 204 and comprising the desired added trait.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, a pea plant of the invention (including transgenic plants, converted plants, hybrid plants and pea plants derived from pea cultivar Sugar 204, and plants produced by the methods of the invention) comprise at least 3, 4, 5, 6, 7, 8, 9, 10 or more of the morphological and physiological characteristics of pea cultivar Sugar 204 (e.g., as described herein, in particular, in Tables 1 to 3), or even all of the morphological and physiological characteristics of pea cultivar Sugar 204, so that said plants are not significantly different for said traits than pea cultivar Sugar 204, as determined at the 5% significance level when grown in the same environmental conditions; optionally, with the presence of one or more desired added traits (e.g., male sterility, disease resistance, pest or insect resistance, herbicide resistance, and the like).

The invention also encompasses plant parts, plant material, pollen, ovules, leaves, berries, pods, shoots and seed from the pea plants of the invention. The invention also provides seed that produces the pea plants of the invention. Also provided is a tissue culture of regenerable cells from the pea plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith, pods, berries and/or capsules; or (b) callus or protoplasts derived from the cells of (a). Further provided are pea plants regenerated from a tissue culture of the invention.

In still yet another aspect, the invention provides a method of determining a genetic characteristic of pea cultivar Sugar 204 or a progeny thereof, e.g., a method of determining a genotype of pea cultivar Sugar 204 or a progeny thereof using molecular techniques. In embodiments, the method comprises detecting in the genome of a Sugar 204 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel pea variety designated Sugar 204.

Those skilled in the art will appreciate that when a comparison of physiological and morphological characteristics between two or more varieties is made, it is assumed that the varieties are grown under the same environmental conditions, whether in the field or green house. In addition, such comparisons are generally made on the basis of observations taken on a population of plants.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

DEFINITIONS

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Afila". Afila is a foliar configuration resulting from the gene 'af', which acts to transform the leaflets on a normal foliage pea to tendrils. Afila plants tend to be more upright in the field than normal foliage peas as the tendrils grab onto one another to hold each other up.

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents (the "recurrent" parent), for example, a first generation hybrid $F_1$ with one of the parental genotypes of the $F_1$ hybrid, e.g., backcrossing 1, 2, 3, 4, 5, 6, 7, 8, 9 or more times to the recurrent parent. The other parental plant is termed the "nonrecurrent" parent, which may also be referred to as the "donor" parent if it contributes a gene(s) for a desired characteristic.

"Cotyledon". One of the first leaves of the embryo of a seed plant; typically one or more in monocotyledons, two in dicotyledons, and two or more in gymnosperms.

"Determinate Plant". A determinate plant will grow to a fixed number of nodes while an indeterminate plant will continue to grow during the season.

"Double haploid line". A stable inbred line achieved by doubling the chromosomes of a haploid line, e.g., from anther culture. For example, some pollen grains (haploid) cultivated under specific conditions develop plantlets containing 1n chromosomes. The chromosomes in these plantlets are then induced to "double" (e.g., using chemical means) resulting in cells containing 2n chromosomes. The progeny of these plantlets are termed "double haploid" and are essentially non-segregating (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of pea cultivar Sugar 204, except for the characteristic(s) derived from a converted locus/loci (e.g., one or more single converted loci), for example, introduced via backcrossing to pea cultivar Sugar 204, a modified gene(s) resulting from genome editing techniques, an introduced transgene (i.e., introduced via genetic transformation techniques), or mutation, when both plants are grown under the same environmental conditions. In embodiments, a plant having "essentially all of the physiological and morphological characteristics" means a plant having all of the characteristics of the reference plant with the exception of five or fewer traits, 4 or fewer traits, 3 or fewer traits, 2 or fewer traits, or one trait. In embodiments, a plant comprising "essentially all of the physiological and morphological characteristics" of pea cultivar Sugar 204 comprises the traits set forth in Tables 1 to 3.

"Field holding ability". A pea plant that has good field holding ability indicates a plant having berries that slowly change in tenderness (e.g., as measured by a tenderometer) over time.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Genetic complement". As used herein, a "genetic complement" refers to the total genetic make-up of the plant.

"Heat unit". The amount of heat needed to mature a crop. It is used to measure maturity based on the daily accumulated heat produced during the growing season. The formula [(daily maximum $F^0$–daily minimum $F^0$)-40]/2 is used to calculate heat units for peas.

"Inbred line". As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Machine harvestable plant". A machine harvestable plant means a pea plant that stands tall and/or upright enough to allow pods and berries to be harvested by machine. The pods can be removed by a machine from the plant without leaves and other plant parts being harvested.

"Maturity date". Plants are considered mature when the pods have reached their maximum desirable berry size and sieve size for the specific use intended.

"Node". A node is the thickened enlargement on a plant. It is where the stipules, leaf and peduncle arise.

"Nodes to 1$^{st}$ flower". The number of nodes to 1$^{st}$ flower is obtained by counting the number of nodes from above the point of cotyledon attachment to the node from which the first peduncle arises.

"Pea plant". As used herein, the term "pea plant" or "pea" includes any plant classified as a *Pisum sativum*. Exemplary pea plants include without limitation shell peas, edible-podded peas (e.g., snap peas, snow peas), and field (dry) peas (e.g., split peas).

"Pea Yield" (Tons/Acre). The yield in tons/acre is the actual yield of the peas at harvest.

"Peduncle". A peduncle is the stalk that bearing flower(s) and subsequent pod(s) arising from a node.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, berries, pods, and the like.

"Plant adaptability". A plant having a good plant adaptability means a plant that will perform well in different growing conditions and seasons.

"Plant Height". Plant height is taken from the top of soil to top-most leaf of the plant.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, pods, berries, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock, pod, berry and/or a fruit including callus and protoplasts derived from any of the foregoing.

"Pod width between the sutures". As used herein, the term "pod width between the sutures" refers to a method of measuring pod width using calipers held on the suture on either side of the pod.

"Sieve Size" (sv). Sieve size is a measure of the diameter of the fresh pea and is commonly used in grading peas. A sieve 1 is a berry that goes through a hole 9⁄32" (7.15 mm) in diameter, a sieve 2 berry goes through a hole 10⁄32" (7.94 mm) in diameter, a sieve 3 berry goes through a hole 11⁄32" (10.32 mm) in diameter, a sieve 4 berry goes through a hole 12⁄32" (9.53 mm), a sieve 5 berry goes through a hole 13⁄32" (10.32 mm), and a sieve 6 and above goes through a hole greater than 13⁄32" (10.32 mm). A sieve size average is calculated by multiplying the percent of peas within each sieve size by the sieve size, summing these products and dividing by 100.

"Tenderometer". A tenderometer is a device for determining the maturity and tenderness of a pea sample.

"Quantitative Trait Loci". A Quantitative Trait Locus (QTL) refers to a genetic locus that controls to some degree, numerically representable traits that are usually continuously distributed (i.e., a quantitative trait).

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A pea plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus conversion". Refers to a modification at a single locus in a plant that convers a trait (e.g., a trait of interest), such as without limitation disease resistance, fertility, sterility, enhanced flowering and the like.

"Single locus converted plant". A single locus converted or conversion plant (and similar terms) refers to a plant that comprises a single locus conversion, which may be introduced by any suitable method known in the art, e.g., by plant breeding techniques (e.g., backcrossing), genome editing techniques, genetic transformation techniques and/or mutation techniques wherein the converted plant comprises the trait converted by the single locus introduced into the plant and otherwise all or essentially all of the morphological and physiological characteristics of the parent plant (e.g., a line).

"Stipules". A pair of leaf-like appendages borne at the base of each pea leaf or stalk.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Botanical Description of Snap Pea Cultivar Sugar 204.

Snap pea cultivar Sugar 204 was developed in Nampa, Idaho, USA, from a hand-pollinated cross between Syngenta proprietary breeding line SP2724-B5-B5-13-1-1-and Syngenta variety Sugar 153 (U.S. Pat. No. 9,603,330), followed by bulk harvesting of the F2 generation and Single Seed Descent breeding for the F3 through F5 generations to fix the lines. The F5 through F8 generations were evaluated for the traits of erect vine, heat tolerance, and pod quality. F8 through F10 generation lines were bulk harvested and designated as SL3204, which was given the commercial denomination Sugar 204. Sugar 204 has the following morphologic and other characteristics, as described in Table 1 below.

TABLE 1

Variety Description Information.

| Trait Name | Value |
|---|---|
| Variety code | SL3204 |
| Multiplication indicator | Open-pollinated |
| Plant height (cm): | 53 (10 cm shorter than Sugar 162) |
| Vine: Habit | Determinate |
| Vine: Branching | None |
| Vine: Internodes | Straight |
| Vine: Stockiness | Medium |
| Leaflets: Color | Medium green |
| Leaflets: Wax | Light |
| Leaflets: Marbling | Not marbled |
| Leaflets: Leaflet type | Semi-leaflet |
| Stipules: Presence | Present |
| Stipules: Marbling | Not marbled |
| Stipules: Size (compared with leaflets) | Larger |
| Stipules: Color (compared with leaflets) | Same |
| Flower color: Venation | White |
| Flower color: Standard | White |
| Flower color: Wing | White |
| Flower color: Keel | White |
| Pods: Shape | Straight |
| Pods: End | Pointed |
| Pods: Texture | Smooth |
| Pods: Luster | Dull |
| Pods: Borne | Single and double |
| Pods: length (cm) | 8 |
| Pods: Width between sutures (mm) | 12 |
| Pods: Number of seeds per pod | 6 |
| Seeds (95-100 Tenderometer): Color | Brown |
| Seeds (dry-mature): Shape | Rounded |
| Seeds (dry-mature): Surface | Smooth |
| Seeds (dry-mature): Hilum color | White |
| Seeds (dry-mature): Cotyledon color | Green |
| Seeds (dry-mature): Hundred seed weight (grams per 100 seeds) | 22 |
| Fusarium wilt - race 1 | Moderately resistant |
| Erysiphe pisi (powdery mildew) | Moderately resistant |
| Peronospora viciae (downy mildew) | Susceptible |
| Pea Enation Mosaic Virus | Susceptible |

Snap pea cultivar Sugar 204 has shown uniformity and stability for the expressed traits, within the limits of environmental influence for the traits. No variant traits have been observed or are expected in snap pea cultivar Sugar 204.

When grown in two different trials during 2022 in Nampa, Idaho, Sugar 204 differs significantly from Sugar 162 in plant height and pod length. All statistical methods were carried out with Statistics 10.0 (Analytical Software, Tallahassee, Florida) and are detailed within the following tables (Tables 2 and 3).

TABLE 2

Plant height comparison of Sugar 204 vs. Sugar 162.

| Variable | N | Mean | SD | Minimum | Maximum |
|---|---|---|---|---|---|
| Sugar 162 | 20 | 63.000 | 0.7255 | 62.000 | 65.000 |
| Sugar 204 | 20 | 54.200 | 1.8806 | 50.000 | 57.000 |

One-Way AOV for: Sugar 162 vs. Sugar 204 on Plant Heights

| Source | DF | SS | MS | F | P |
|---|---|---|---|---|---|
| Between | 1 | 774.400 | 774.400 | 381.18 | 0.0000 |
| Within | 38 | 77.200 | 2.032 | | |
| Total | 39 | 851.600 | | | |
| Grand Mean | 58.600 | CV 2.43 | | | |

| Homogeneity of Variances | F | P |
|---|---|---|
| Levene's Test | 8.31 | 0.0064 |
| O'Brien's Test | 7.87 | 0.0079 |
| Brown and Forsythe Test | 14.93 | 0.0004 |

Welch's Test for Mean Differences

| Source | DF | F | P |
|---|---|---|---|
| Between | 1.0 | 381.18 | 0.0000 |
| Within | 24.5 | | |

| | |
|---|---|
| Component of variance for between groups | 38.6184 |
| Effective cell size | 20.0 |

| Variable | Mean |
|---|---|
| Sugar 162 | 63.000 |
| Sugar 204 | 54.200 |
| Observations per Mean | 20 |
| Standard Error of a Mean | 0.3187 |
| Std Error (Diff of 2 Means) | 0.4507 |

LSD All-Pairwise Comparisons Test on Plant Heights

| Variable | Mean | Homogeneous Groups |
|---|---|---|
| Sugar 162 | 63.000 | A |
| Sugar 204 | 54.200 | B |

| | | |
|---|---|---|
| Alpha | 0.05 | Standard Error for Comparison 0.4507 |
| Critical T Value | 2.024 | Critical Value for Comparison 0.9125 |

All 2 means are significantly different from one another.

TABLE 3

Pod length comparison of Sugar 204 vs. Sugar 162.

| Variable | N | Mean | SD | Minimum | Maximum |
|---|---|---|---|---|---|
| Sugar 162 | 20 | 9.3900 | 0.3161 | 8.6000 | 10.000 |
| Sugar 204 | 20 | 8.0500 | 0.1147 | 7.9000 | 8.2000 |

One-Way AOV for: Sugar 162 vs. Sugar 204 on Pod Length

| Source | DF | SS | MS | F | P |
|---|---|---|---|---|---|
| Between | 1 | 17.9560 | 17.9560 | 317.66 | 0.0000 |
| Within | 38 | 2.1480 | 0.0565 | | |
| Total | 39 | 20.1040 | | | |
| Grand Mean | 8.7200 | CV 2.73 | | | |

TABLE 3-continued

Pod length comparison of Sugar 204 vs. Sugar 162.

| Homogeneity of Variances | F | P |
|---|---|---|
| Levene's Test | 5.59 | 0.0233 |
| O'Brien's Test | 5.29 | 0.0270 |
| Brown and Forsythe Test | 8.94 | 0.0049 |

Welch's Test for Mean Differences

| Source | DF | F | P |
|---|---|---|---|
| Between | 1.0 | 317.66 | 0.0000 |
| Within | 23.9 | | |

| | |
|---|---|
| Component of variance for between groups | 0.89497 |
| Effective cell size | 20.0 |

| Variable | Mean |
|---|---|
| Sugar 162 | 9.3900 |
| Sugar 204 | 8.0500 |
| Observations per Mean | 20 |
| Standard Error of a Mean | 0.0532 |
| Std Error (Diff of 2 Means) | 0.0752 |

LSD All-Pairwise Comparisons Test on Pod Length

| Variable | Mean | Homogeneous Groups |
|---|---|---|
| Sugar 162 | 9.3900 | A |
| Sugar 204 | 8.0500 | B |

| | | |
|---|---|---|
| Alpha | 0.05 | Standard Error for Comparison 0.0752 |
| Critical T Value | 2.024 | Critical Value for Comparison 0.1522 |

All 2 means are significantly different from one another.

Tissue Culture.

In embodiments, pea plants can be propagated by tissue culture and regeneration. Tissue culture of various plant tissues and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28 (2), 139-145 (1992). It is clear from the literature that the state of the art is such that these methods of obtaining plants are routinely used and have a very high rate of success. Thus, another aspect of this invention is to provide cells which upon growth and differentiation produce pea plants having desired characteristics of pea cultivar Sugar 204. \Optionally, pea plants can be regenerated from the tissue culture of the invention comprising all or essentially all of the physiological and morphological characteristics of pea cultivar Sugar 204.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a pea plant by crossing a first parent pea plant with a second parent pea plant wherein the first and/or second parent pea plant is a plant of pea cultivar Sugar 204. Thus, any of the following exemplary methods using pea cultivar Sugar 204 are part of this invention: selfing, open pollinations, backcrosses, hybrid production, crosses to populations, double haploid production, and the like. All plants produced using pea cultivar Sugar 204 as at least one parent are within the scope of this invention, including those developed from pea plants derived from pea cultivar Sugar 204. Advantageously, pea cultivar Sugar 204 can be used in crosses with other, different, pea plants to produce the first generation $(F_1)$ pea hybrid seeds and plants with desirable characteristics. The pea plants of the invention can also be used for transformation where exogenous transgenes are introduced and expressed by the plants of the invention. Genetic variants created either through traditional breeding methods, genome editing techniques, mutagenesis or through transformation of the cultivars of the invention by any of a number of protocols known to those of skill in the art are intended to be within the scope of this invention.

The following describes exemplary breeding methods that may be used with pea cultivar Sugar 204 in the development of further pea plants. One such embodiment is a method for developing pea cultivar Sugar 204 progeny pea plants in a pea plant breeding program comprising: obtaining a plant, or a part thereof, of pea cultivar Sugar 204, utilizing said plant or plant part as a source of breeding material, and selecting a pea cultivar Sugar 204 progeny plant, e.g., with molecular markers in common with pea cultivar Sugar 204 and/or with some, essentially all, or all of the morphological and/or physiological characteristics of pea cultivar Sugar 204 (see, e.g., Tables 1 to 3). In representative embodiments, the progeny plant has at least 1, 2, 3, 4, 5, 6, 7, 8, 9, 10 or more of the morphological and physiological characteristics of pea cultivar Sugar 204 (e.g., as described in Tables 1 to 3), or even all of the morphological and physiological characteristics of pea cultivar Sugar 204 so that said progeny pea plant is not significantly different for said traits than pea cultivar Sugar 204, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of pea cultivar Sugar 204 progeny plants, comprising crossing pea cultivar Sugar 204 with another pea plant, thereby producing a population of pea plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pea cultivar Sugar 204, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pea cultivar Sugar 204. One embodiment of this invention is the pea plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from pea cultivar Sugar 204, and optionally is the result of a breeding process comprising one or two breeding crosses and as a further option, one or more of selfing, sibbing, backcrossing and/or double haploid techniques in any combination and any order. In embodiments, the breeding process does not include a breeding cross, and comprises selfing, sibbing, backcrossing and or double haploid techniques in any combination and any order. A plant of this population may be selected and repeatedly selfed or sibbed with a pea plant resulting from these successive filial generations. Another approach is to make double haploid plants to achieve homozygosity. In embodiments, the breeding process does not include a breeding cross, and optionally comprises selfing, sibbing, backcrossing and/or double haploid techniques.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the invention encompasses Sugar 204 progeny plants having a combination of at least 2, 3, 4, 5, 6, 7, 8, 9, 10 or more of the characteristics as described herein for pea cultivar Sugar 204, so that said progeny pea plant is not significantly different for said traits than pea cultivar Sugar 204, as determined at the 5% significance level when grown in the same environmental conditions. Using techniques described herein and those known in the art, molecular markers may be used to identify said progeny plant as progeny of pea cultivar Sugar 204. Mean trait values may be used to determine whether trait differences are significant, and optionally the traits are measured on plants grown under the same environmental conditions.

Progeny of pea cultivar Sugar 204 may also be characterized through their filial relationship with pea cultivar Sugar 204, as for example, being within a certain number of breeding crosses of pea cultivar Sugar 204. A breeding cross is a cross made to introduce new genetics into the progeny, and is distinguished from a cross, such as a self or a sib cross or a backcross to Sugar 204 as a recurrent parent, made to select among existing genetic alleles. The lower the number of breeding crosses in the pedigree, the closer the relationship between pea cultivar Sugar 204 and its progeny. For example, progeny produced by the methods described herein may be within 1, 2, 3, 4, 5 or more breeding crosses of pea cultivar Sugar 204.

In representative embodiments, a pea plant derived from pea cultivar Sugar 204 comprises cells comprising at least one set of chromosomes derived from pea cultivar Sugar 204.

In embodiments, a pea plant or population of pea plants derived from pea cultivar Sugar 204 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pea cultivar Sugar 204, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pea cultivar Sugar 204, and optionally may be the result of one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the pea plant derived from pea cultivar Sugar 204 is one, two, three, four, five or more breeding crosses removed from pea cultivar Sugar 204.

In representative embodiments, a plant derived from pea cultivar Sugar 204 is a double haploid plant, a hybrid plant or an inbred plant.

In embodiments, a derived plant from pea cultivar Sugar 204 comprises a desired added trait. In representative embodiments, a pea plant derived from pea cultivar Sugar 204 comprises the desired added trait and otherwise all or essentially all of the morphological and physiological characteristics of pea cultivar Sugar 204 (e.g., as described in Tables 1 to 3).

Those skilled in the art will appreciate that any of the traits described above with respect to plant transformation methods can be introduced into a plant of the invention (e.g., pea cultivar Sugar 204 and hybrid pea plants and other pea plants derived therefrom) using breeding techniques.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as “transgenes.” Numerous methods for producing transgenic plants have been developed, and in particular embodiments the present invention also relates to transformed versions of pea plants disclosed herein.

Genetic engineering techniques can be used (alone or in combination with breeding methods) to introduce one or more desired added traits into plant, for example, pea cultivar Sugar 204 or progeny or plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed plants using transformation methods as described herein to incorporate transgenes into the genetic material of the plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for gene editing techniques.

Any transgene, including those exemplified above, can be introduced into the plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic line. The transgenic line can then be crossed with another (non-transgenic or transgenic) line in order to produce a new transgenic line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Genome Editing.

Genome editing methodologies are known in the art and can be carried out by any suitable technique. For example, targeted genome editing can be done using CRISPR/Cas9 technology (Saunders & Joung, *Nature Biotechnology,* 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. J. Bacteriol. 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. (Barrangou, R., et al. *Science* 315, 1709-1712 (2007)). Many plants have already been modified using the CRISPR system. See for example, U.S. Application Publication No. WO2014068346 (Gyorgy et al., Identification of a *Xanthomonas* euvesicatoria resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science* Vol. 7 Nov. 2016; and "Exploiting the CRISPR/Cas9 System for Targeted Genome Mutagenesis in Petunia" *Science Reports* Volume 6: February 2016.

Genome editing can also be done using crRNA-guided surveillance systems for genome editing. Additional information about crRNA-guided surveillance complex systems for genome editing can be found in the following documents: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34:1473-1476. Therefore, the invention also contemplates using genome editing on pea cultivar Sugar 204 to modify traits of interest including without limitation disease resistance, insect resistance, nematode resistance, herbicide resistance, flowering, fertility, sterility, and the like.

Locus Conversion.

The term "locus converted plant", "converted plant", or plant having a "locus conversion" (and similar terms) as used herein refers to those plants that are developed, for example, by backcrossing, genome editing, genetic transformation and/or mutation (e.g., into a parental line), wherein essentially all of the desired morphological and physiological characteristics of a variety are recovered in addition to the one or more converted loci introduced into the plant. To illustrate, in particular embodiments, backcrossing into a parental line can be used with the present invention to improve or introduce a characteristic into the variety. The gene/locus that is transferred can be a native gene/locus, a mutated native gene/locus or a transgene introduced by genetic engineering techniques into the plant (or ancestor thereof). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Pea Cultivar Sugar 204.

The invention further provides a method of determining a genetic characteristic of pea cultivar Sugar 204 or a progeny thereof, e.g., a method of determining a genotype of pea cultivar Sugar 204 or a progeny thereof. In embodiments, the method comprises detecting in the genome of a Sugar 204 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism (e.g., a Single Nucleotide Polymorphism [SNP]) in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT INFORMATION

Applicants have made a deposit of at least 625 seeds of snap pea cultivar Sugar 204 under the denomination SL3204 with the Provasoli-Guillard National Center for Marine Algae and Microbiota (NCMA) at Bigelow Laboratory for Ocean Sciences, 60 Bigelow Drive, East Boothbay, Me., 04544 U.S.A. under NCMA Accession No. 202502030 on Feb. 21, 2025 This deposit of snap pea variety Sugar 204 will be maintained in the NCMA depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 625 seeds of the variety with the NCMA. Applicants will impose no restrictions on the availability of the deposited material from the NCMA; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant inbred and the like may be practiced within the scope of the invention.

What is claimed is:

1. A seed of pea cultivar Sugar 204, a representative sample of seed of said cultivar having been deposited under NCMA Accession No. 202502030.

2. A plant of pea cultivar Sugar 204, a representative sample of seed of said pea cultivar having been deposited under NCMA Accession No. 202502030.

3. A pea plant, or a part thereof, having all of the physiological and morphological characteristics of the pea plant of claim 2.

4. A plant part of the pea plant of claim 2.

5. The plant part of claim 4, wherein the plant part is a pod, a berry, pollen, an ovule, or a cell.

6. A tissue culture of regenerable cells of the plant of claim 2.

7. A pea plant regenerated from the tissue culture of claim 6, wherein said pea plant comprises all of the physiological and morphological characteristics of pea cultivar Sugar 204.

8. A converted pea plant produced by introducing a single locus conversion into the plant of claim 2, wherein said converted pea plant comprises said single locus conversion and otherwise comprises all of the physiological and morphological characteristics of pea cultivar Sugar 204.

9. A processed product from the plant of claim 2, wherein said processed product comprises dehydrated, cut, sliced, ground, pureed, dried, canned, jarred, washed, brined, packaged, refrigerated, frozen and/or heated pods, berries or seeds.

10. A method of producing seed, the method comprising selfing the plant of claim 2 or crossing the plant of claim 2 with another pea plant and harvesting the resulting seed.

11. An F1 seed produced by the method of claim 10.

12. An F1 plant produced by growing the seed of claim 10.

13. A method for producing a seed of a pea plant derived from the plant of claim 2, the method comprising:

(a) crossing a plant of pea cultivar Sugar 204, a representative sample of seed of said pea cultivar having been deposited under NCMA Accession No. 202502030, with a second pea plant;

(b) allowing seed to form;

(c) growing a plant from the seed of step (b) to produce a plant derived from pea cultivar Sugar 204;

(d) selfing the plant of step (c) or crossing it to a second pea plant to form additional pea seed derived from pea cultivar Sugar 204; and (e) optionally repeating steps (c) and (d) one or more times to generate further derived pea seed from pea cultivar Sugar 204, wherein in step (c) a plant is grown from the additional pea seed of step (d) in place of growing a plant from the seed of step (b).

14. A method of vegetatively propagating the plant of claim 2, the method comprising:

(a) collecting tissue capable of being propagated from a plant of pea cultivar Sugar 204, a representative sample of seed of said pea cultivar having been deposited under NCMA Accession No. 202502030;

(b) cultivating the tissue to obtain proliferated shoots;

(c) rooting the proliferated shoots to obtain rooted plantlets; and (d) optionally, growing plants from the rooted plantlets.

15. Plantlets or plants obtained by the method of claim 14.

16. A method of introducing a desired added trait into pea cultivar Sugar 204, the method comprising:

(a) crossing the plant of claim 2 with a pea plant that comprises a desired added trait to produce F1 progeny;

(b) selecting an F1 progeny that comprises the desired added trait;

(c) crossing the selected F1 progeny with pea cultivar Sugar 204 to produce backcross progeny;

(d) selecting backcross progeny comprising the desired added trait; and (e) repeating steps (c) and (d) one or more times to produce a plant derived from pea cultivar Sugar 204 comprising the desired added trait and otherwise all of the physiological and morphological characteristics of pea cultivar Sugar 204, wherein in step (c) the selected backcross progeny produced in step (d) is used in place of the selected F1 progeny of step (b).

17. The method of claim 16, wherein the desired added trait is male sterility, pest resistance, insect resistance, disease resistance, herbicide resistance, or any combination thereof.

18. A single locus converted pea plant produced by the method of claim 16, wherein the pea plant has the desired added trait and otherwise all of the physiological and morphological characteristics of pea cultivar Sugar 204.

19. Seed of the plant of claim 18, wherein the seed produces a pea plant that has the desired added trait and otherwise all of the physiological and morphological characteristics of pea cultivar Sugar 204.

20. A method of producing a plant of pea cultivar Sugar 204 comprising a desired added trait, the method comprising introducing a transgene conferring the desired added trait into the plant of claim 2.

21. A single locus converted pea plant produced by the method of claim 20 comprising the desired added trait and otherwise all of the physiological and morphological characteristics of pea cultivar Sugar 204.

22. Seed of the plant of claim 21, wherein the seed produces a plant comprising the desired added trait and otherwise all of the physiological and morphological characteristics of pea cultivar Sugar 204.

23. A method of producing a pea pod from pea cultivar Sugar 204, the method comprising:

(a) growing the pea plant according to claim 2 to produce a pea pod; and (b) harvesting the pea pod.

24. A method of producing a processed product from pea cultivar Sugar 204, the method comprising:

(a) obtaining a pod of the plant of claim 2; and (b) processing said pod to produce a processed product.

* * * * *